US011957490B2

(12) United States Patent
Huhta et al.

(10) Patent No.: US 11,957,490 B2
(45) Date of Patent: Apr. 16, 2024

(54) DYNAMIC ADJUSTMENTS OF PHYSIOLOGICAL DATA

(71) Applicant: Medtronic MiniMed, Inc., Northridge, CA (US)

(72) Inventors: Brent A. Huhta, Big Lake, MN (US); Jake T. Roerig, Fridley, MN (US); Brandon J. Plantage, Eden Prairie, MN (US); Melonie Hedlund, Excelsior, MN (US); Christine D. Schulz, Hudson, WI (US)

(73) Assignee: Medtronic MiniMed, Inc., Northridge, CA (US)

( * ) Notice: Subject to any disclaimer, the term of this patent is extended or adjusted under 35 U.S.C. 154(b) by 152 days.

(21) Appl. No.: 17/590,088

(22) Filed: Feb. 1, 2022

(65) Prior Publication Data

US 2022/0240867 A1 Aug. 4, 2022

Related U.S. Application Data

(60) Provisional application No. 63/144,897, filed on Feb. 2, 2021.

(51) Int. Cl.
*A61B 5/00* (2006.01)
*A61B 5/145* (2006.01)
*G16H 10/60* (2018.01)

(52) U.S. Cl.
CPC .......... *A61B 5/743* (2013.01); *A61B 5/14532* (2013.01); *A61B 5/7475* (2013.01); *G16H 10/60* (2018.01)

(58) Field of Classification Search
None
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

OTHER PUBLICATIONS

Plougmann, Søren, Ole K. Hejlesen, and David A. Cavan. "DiasNet—a diabetes advisory system for communication and education via the internet." International Journal of Medical Informatics 64.2-3 (2001): 319-330. (Year: 2001).*

(Continued)

*Primary Examiner* — Nurun Flora
(74) *Attorney, Agent, or Firm* — Weaver Austin Villeneuve & Sampson LLP (57) ABSTRACT

Disclosed are techniques including accessing historical physiological data of a person; presenting a graph view of a historical time period, where the graph view includes at least a portion of the historical physiological data plotted over the historical time period and includes one or more historical events which occurred during the historical time period; receiving user input indicative of a marker for an event, of the one or more historical events, being adjusted from a first position in the historical time period to a second position in the historical time period; responsive to receiving the user input, accessing adjusted physiological data for the person from at least the time point in the historical time period to an end of the historical time period, where the adjusted physiological data has been determined based on the adjusted marker for the event marker and a physiological model for the person; and presenting the adjusted physiological data.

18 Claims, 4 Drawing Sheets

(56) References Cited

U.S. PATENT DOCUMENTS

| | | | |
|---|---|---|---|
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Nunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,974,385 B2 | 3/2015 | Lee et al. | |
| 9,672,328 B2 | 6/2017 | Saint et al. | |
| 10,182,748 B2 | 1/2019 | Catt et al. | |
| 10,835,727 B2 | 11/2020 | Montalvo et al. | |
| 2007/0123819 A1 | 5/2007 | Mernoe et al. | |
| 2010/0160861 A1 | 6/2010 | Causey et al. | |
| 2015/0289821 A1 | 10/2015 | Rack-Gomer et al. | |
| 2018/0042558 A1 | 2/2018 | Cabrera, Jr. et al. | |
| 2019/0298259 A1 | 10/2019 | Mensinger et al. | |
| 2020/0012265 A1* | 1/2020 | Thomsen | G06F 3/0481 |
| 2020/0146598 A1 | 5/2020 | Mayou et al. | |
| 2020/0327973 A1 | 10/2020 | Pryor et al. | |

OTHER PUBLICATIONS

International Search Report dated May 17, 2022 and Written Opinion completed May 6, 2022 corresponding to counterpart Int'l Patent Application PCT/US2022/014717.

Plougmann et al: "DiasNet-a diabetes advisory system for communication and education via the internet", International Journal of Medical Informatics, Elsevier Scientific Publishers, Shannon, IR, vol. 64, No. 2-3, Dec. 31, 2001 (Dec. 31, 2001), pp. 319-330, XP004329219, ISSN: 1386-5056, DOI:10.1016/S1386-5056(01)00214-3, abstract p. 321-p. 326, sections 3.1-3.4, figures 1-6.

Franklin V. L. et al: "A predictive tool for the self-management of diabetes (Librae): evaluation using a continuous glucose monitoring system", Diabetic Medicine., vol. 23, No. 1, Jan. 31, 2006 (Jan. 31, 2006), pp. 21-25, XP055918254,GB ISSN: 0742-3071, DOI: 10.1111/j.1464-5491.2005.01770.x abstract, p. 22-p. 23, figure 1.

* cited by examiner

DYNAMIC ADJUSTMENTS OF PHYSIOLOGICAL DATA

CROSS-REFERENCE TO RELATED APPLICATIONS

The present application claims the benefit of, and priority to, U.S. Provisional Application No. 63/144,897, filed Feb. 2, 2021, the entire contents of which are hereby incorporated by reference herein in its entirety.

TECHNICAL FIELD

The present disclosure relates generally to the medical arts and, more specifically, to dynamic adjustments of physiological data.

BACKGROUND

Therapy devices and systems may be used to treat various health conditions. For example, insulin infusion and glucose monitoring devices and systems may facilitate management of diabetes for some persons. Such therapy devices and systems may store information relating to the therapy and its administration, and such information may be useful for various purposes.

SUMMARY

Disclosed herein are techniques related to dynamic adjustments of physiological data. The techniques may be practiced using a processor-implemented method; a device comprising one or more processors and one or more processor-readable storage media; and one or more non-transitory processor-readable storage media.

In some embodiments, the techniques involve accessing historical physiological data of a person and presenting, on a display screen, a graph view of a historical time period. The graph view includes at least a portion of the historical physiological data plotted over the historical time period and includes one or more historical events which occurred during the historical time period. The techniques further involve receiving user input indicative of a marker for an event, among the one or more historical events, being adjusted from a first position in the historical time period to a second position in the historical time period. The second position corresponds to a time point in the historical time period. The techniques also involve accessing, responsive to receiving the user input adjusted physiological data for the person from the time point in the historical time period to an end of the historical time period. The adjusted physiological data is determined based on the adjusted marker for the event and a physiological model for the person. Additionally, the techniques involve presenting, on the display screen, the adjusted physiological data.

BRIEF DESCRIPTION OF THE DRAWINGS

The above and other aspects and features of the disclosure will become more apparent in view of the following detailed description when taken in conjunction with the accompanying drawings wherein like reference numerals identify similar or identical elements.

DETAILED DESCRIPTION

Graphical user interfaces (GUIs) are popular for conveying physiological data (e.g., glucose concentration values) in a visual format that can be readily understood. As the saying goes, "a picture is worth a thousand words," so it is not surprising that many healthcare providers (e.g., physicians) use GUIs to provide feedback to patients regarding the effectiveness of various therapies. However, GUIs typically convey information in a static format. For example, historical data is often presented as an immutable record of the past. As such, patients tend to believe there is little that could have been done differently.

Disclosed herein are example techniques related to dynamic adjustments of physiological data. In some embodiments, GUIs may be configured to demonstrate the effects of hypothetical changes in behavior based on dynamically displaying adjustments to historical data. For example, the dramatic impact of administering medicine just a few minutes earlier can be immediately communicated to a patient in a compelling manner. In a sense, such GUIs enable patients to travel back in time and see how taking certain actions could have altered history.

The present disclosure is described primarily with respect to insulin delivery systems. Aspects and embodiments of the present disclosure can be practiced with one or more types of insulin (e.g., fast-acting insulin, intermediate-acting insulin, and/or slow-acting insulin). Unless indicated by the context, terms such as "dose," "insulin," "basal," and "bolus" may not denote a particular type of insulin. For example, fast-acting insulin may be used for both basal dosages and bolus dosages. As used herein, the term "basal" refers to and includes insulin that is delivered in an amount and at a frequency that is intended to correspond to a healthy body's release of insulin between meals and during sleep. The term "bolus" refers to and includes insulin that is delivered in an amount and at a timing that is intended to correspond to a healthy body's release of insulin for counteracting a high glucose level, such as that caused by consumption of a meal. A meal may include any type or amount of food or beverage consumption, including breakfast, lunch, dinner, snacks, and beverages, among others.

Although the present disclosure may be described primarily with respect to insulin delivery systems, the scope of the present disclosure is not limited to insulin delivery systems. Rather, the present disclosure applies to and can be implemented for other therapy systems as well. It is intended that any aspects, embodiment, and description relating to insulin delivery systems shall be applicable to other types of therapy delivery systems as well.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other non-transitory information storage media that may store instructions to perform operations and/or processes. As used herein, "exemplary" does not necessarily mean "preferred" and may simply refer to an example unless the context clearly indicates otherwise. Although the disclosure is not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term "set" when used herein may include one or more items. Unless explicitly stated, the methods described herein are not constrained to a particular order or sequence. Additionally, some of the described methods or elements thereof can occur or be performed simultaneously, at the same point in time, or concurrently.

Figure 1:
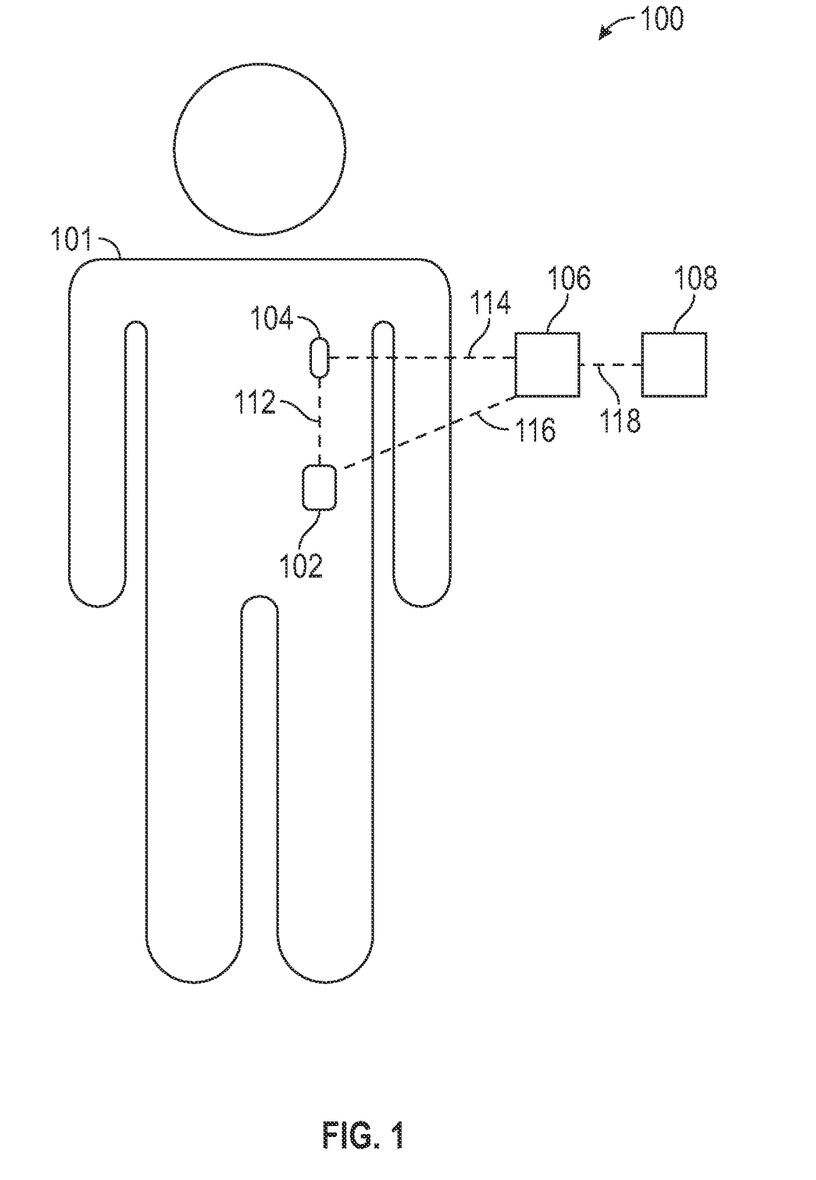
FIG. 1 is a diagram of an exemplary system in accordance with aspects of the present disclosure.

Referring to FIG. 1, there is shown a diagram of an exemplary therapy delivery system 100 for a person 101. System 100 may be an insulin delivery system. The illustrated therapy delivery system 100 includes a delivery device 102, a monitoring device 104, a computing device 106, and an optional remote or cloud computing system 108. The delivery device 102, the monitoring device 104, and the computing device 106 may be embodied in various ways, including being disposed in one or more device housings. For example, in various embodiments, all of the devices 102-106 may be disposed in a single device housing. In various embodiments, each of the devices 102-106 may be disposed in a separate device housing. In various embodiments, two or more of the devices 102-106 may be disposed in the same device housing, and/or a single device 102, 104, or 106 may have two or more parts that are disposed in two or more housings. Such embodiments, and combinations thereof, are contemplated to be within the scope of the present disclosure.

FIG. 1 also illustrates communications links 112-118. The communications links 112-118 may each be a wired connection and/or a wireless connection. In the case where two devices are located in the same device housing, the communication link may include, for example, wires, cables, and/or communication buses on a printed circuit board, among other things. In the case where two devices are separated from each other in different device housings, the communication links may be wired and/or wireless connections. Wired connections may include, without limitation, an Ethernet connection, a USB connection, and/or another type of physical connection. Wireless connections may include, without limitation, a cellular connection, a Wi-Fi connection, a Bluetooth® connection, a mesh network connection, and/or another type of connection using a wireless communication protocol. Various embodiments of the communication links 112-118 may use direct connections, such as Bluetooth® connections, and/or may use connections that route through one or more networks or network devices (not shown), such as an Ethernet network, a Wi-Fi network, a cellular network, a satellite network, an intranet, an extranet, the Internet, and/or the Internet backbone, among other types of networks. Various combinations of wired and/or wireless connections may be used for the communication links 112-118.

Aspects of the insulin delivery system 100 are described below. Further aspects and details may be described in U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893. The entire contents of each of the foregoing United States Patents are hereby incorporated by reference herein.

The delivery device 102 is configured to deliver a therapeutic substance (e.g., insulin) to a person 101. The delivery device 102 may be secured to the person 101 (e.g., to the body or clothing of the person 101) or may be implanted on or in the body of the person 101. In various embodiments, the delivery device 102 may include a reservoir, an actuator, a delivery mechanism, and a cannula (not shown). The reservoir may be configured to store an amount of the therapeutic substance. In various embodiments, the reservoir may be refillable or replaceable. The actuator may be configured to drive the delivery mechanism. In some examples, the actuator may include a motor, such as an electric motor. The delivery mechanism may be configured to move the therapeutic substance from the reservoir through the cannula. In some examples, the delivery mechanism may include a pump and/or a plunger. The cannula may facilitate a fluidic connection between the reservoir and the body of the person 101. The cannula and/or a needle may facilitate delivery of the therapeutic substance to a tissue layer, vein, or body cavity of the person 101. During operation, the actuator, in response to a signal (e.g., a command signal), may drive the delivery mechanism, thereby causing the therapeutic substance to move from the reservoir, through the cannula, and into the body of the person 101.

The components of the delivery device 102 described above are exemplary. The delivery device 102 may include other components, such as, without limitation, a power supply, a communication transceiver, computing resources, and/or user interfaces, among other things. Persons skilled in the art will recognize various implementations of the delivery device 102 and the components of such implementations. All such implementations and components are contemplated to be within the scope of the present disclosure.

With continuing reference to FIG. 1, the monitoring device 104 is configured to detect a physiological condition (e.g., a glucose concentration level) of the person 101 and may also be configured to detect other things. The monitoring device 104 may be secured to the body of the person 101 (e.g., to the skin of person 101 via an adhesive) and/or may be at least partially implanted into the body of the person 101. Depending on the particular location or configuration, the monitoring device 104 may be in contact with biological matter (e.g., interstitial fluid and/or blood) of the person 101.

The monitoring device 104 includes one or more sensors (not shown), such as, without limitation, electrochemical sensors, electrical sensors, and/or optical sensors. As persons skilled in the art will understand, an electrochemical sensor may be configured to respond to the interaction or binding of a biological marker to a substrate by generating an electrical signal based on a potential, conductance, and/or impedance of the substrate. The substrate may include a material selected to interact with a particular biomarker, such as glucose. The potential, conductance, and/or impedance may be proportional to a concentration of the particular biomarker. In the case of electrical sensors, and as persons skilled in the art will understand, an electrical sensor may be configured to respond to an electrical biosignal by generating an electrical signal based on an amplitude, frequency, and/or phase of the electrical biosignal. The electrical biosignal may include a change in electric current produced by the sum of an electrical potential difference across a tissue, such as the nervous system, of the person 101. In various embodiments, the electrical biosignal may include portions of a potential change produced by the heart of the person 101 over time, e.g., recorded as an electrocardiogram, that are indicative of a glucose level of the person 101. In the case of optical sensors, as persons skilled in the art will understand, an optical sensor may be configured to respond to the interaction or binding of a biological marker to a substrate by generating an electrical signal based on change in luminance of the substrate. For example, the substrate may include a material selected to fluoresce in response to contact with a selected biomarker, such as glucose. The fluorescence may be proportional to a concentration of the selected biomarker.

In various embodiments, the monitoring device 104 may include other types of sensors that may be worn, carried, or coupled to the person 101 to measure activity of the person 101 that may influence the glucose levels or glycemic response of the person 101. As an example, the sensors may include an acceleration sensor configured to detect an acceleration of the person 101 or a portion of the person 101, such as the person's hands or feet. The acceleration (or lack thereof) may be indicative of exercise, sleep, or food/beverage consumption activity of the person 101, which may influence the glycemic response of the person 101. In various embodiments, the sensors may include heart rate and/or body temperature, which may indicate an amount of physical exertion experienced by the person 101. In various embodiments, the sensors may include a GPS receiver which detects GPS signals to determine a location of the person 101.

The sensors described above are exemplary. Other sensors or types of sensors for monitoring physiological condition, activity, and/or location, among other things, will be recognized by persons skilled in the art and are contemplated to be within the scope of the present disclosure. For any sensor, the signal provided by a sensor shall be referred to as a "sensor signal."

The monitoring device 104 may include components and/or circuitry configured to preprocess sensor signals. Preprocessing may include, without limitation, amplification, filtering, attenuation, scaling, isolation, normalization, transformation, sampling, and/or analog-to-digital conversion, among other things. Persons skilled in the art will recognize various implementations for such preprocessing, including, without limitation, implementations using processors, controllers, ASICS, integrated circuits, hardware, firmware, programmable logic devices, and/or machine-executable instructions, among others. The types of preprocessing and their implementations are exemplary. Other types of preprocessing and implementations are contemplated to be within the scope of the present disclosure. In various embodiments, the monitoring device 104 may not perform preprocessing.

As used herein, the term "sensed data" shall mean and include the information represented by a sensor signal or by a preprocessed sensor signal. In various embodiments, sensed data may include glucose levels in a person 101, acceleration of a part of the person 101, heart rate and temperature of the person 101, and/or GPS location of the person 101, among other things. The monitoring device 104 may communicate sensed data to the delivery device 102 via communication link 112 and/or to the computing device 106 via communication link 114. Use of sensed data by the delivery device 102 and/or by the computing device 106 will be described below.

The computing device 106 provides processing capabilities and may be implemented in various ways. In various embodiments, the computing device 106 may be a consumer device, such as a smartphone, a computerized wearable device (e.g., a smartwatch), a tablet computer, a laptop computer, or a desktop computer, among others, or may be a special purpose device (e.g., a portable control device) provided by, for example, the manufacturer of the delivery device 102. In various embodiments, the computing device 106 may be "processing circuitry" (defined below) that is integrated with another device, such as the delivery device 102. In various embodiments, the computing device 106 may be secured to the person 101 (e.g., to the body or clothing of person 101), may be at least partially implanted into the body of person 101, and/or may be held by the person 101.

For each of the embodiments of the computing device 106, the computing device 106 may include various types of logic circuitry, including, but not limited to, microprocessors, controllers, digital signal processors (DSPs), application specific integrated circuits (ASICs), field-programmable gate arrays (FPGAs), central processing units (CPU), graphics processing units (GPU), programmable logic devices, memory (e.g., random access memory, volatile memory, non-volatile memory, etc.), or other discrete or integrated logic circuitry, as well as combinations of such components. The term "processing circuitry" may generally refer to any of the foregoing logic circuitry, alone or in combination with other logic circuitry, or any other circuitry for performing computations.

Aspects of the delivery device 102, the monitoring device 104, and the computing device 106 have been described above. One or more of the devices 102-106 may include a user interface (not shown) that presents information to the person 101 and/or receives information from the person 101. The user interface may include a graphical user interface (GUI), a display device, a keyboard, a touchscreen, a speaker, a microphone, a vibration motor, buttons, switches, and/or other types of user interfaces. Persons skilled in the art will recognize various types of user interfaces that may be used, and all such user interfaces are contemplated to be within the scope of the present disclosure. For example, where the computing device 106 is a consumer device such as a smart phone, tablet computer, laptop computer, or the like, the user interfaces would include a display device, a physical and/or virtual keyboard, and/or audio speakers provided by such consumer devices, among other things. In various embodiments, a user interface may notify the person 101 of sensed data (e.g., glucose level) and/or insulin delivery data (e.g., rates of historic, current, or future insulin delivery) and may present alerts to the person 101. In various embodiments, a user interface may receive inputs from the person 101, which may include, for example, a requested change in insulin delivery and/or a meal indication, among other things. The descriptions and embodiments above regarding user interfaces are exemplary, and other types and other uses of user interfaces are contemplated to be within the scope of the present disclosure.

The following describes communications between the devices 102-106 and cooperation between the devices 102-106 with respect to insulin delivery. As illustrated in FIG. 1, and as mentioned above, the devices 102-106 may communicate with each other via communication links 112-116. In various embodiments, the computing device 106 may control operation of the delivery device 102 and/or the monitoring device 104. For example, the computing device 106 may generate one or more signals (e.g., a command signal) that cause the delivery device 102 to deliver insulin to the person 101, e.g., as a basal dosage and/or a bolus dosage. In various embodiments, the computing device 106 may receive data associated with insulin delivery (e.g., insulin delivery data) from the delivery device 102 and/or receive sensed data (e.g., glucose levels) from the monitoring device 104 and may perform computations based on the insulin delivery data, the sensed data, and/or other data to control the delivery device 102. Insulin delivery data may include, but is not limited to, a type of insulin being delivered, historical insulin delivery rates and/or amounts, current insulin delivery rate and/or amount, and/or user input affecting insulin delivery. As persons skilled in the art will understand, in a closed-loop operating mode, computing device 106 may communicate dosage commands to the delivery device 102 based on a difference between a current glucose level in the body of the person 101 (e.g., received from the monitoring device 104) and a target glucose level (e.g., determined by the computing device 106). The dosage commands may indicate an amount of insulin to be delivered and/or a rate of insulin delivery and may regulate the current glucose level toward the target glucose level. Examples of closed-loop operations for insulin infusion systems are described in U.S. Pat. Nos. 6,088,608, 6,119,028, 6,589,229, 6,740,072, 6,827,702, 7,323,142, and 7,402,153, and in U.S. Patent Application Publication Nos.: 2014/0066887 and 2014/0066889. The entire contents of each of the foregoing patents and publications are hereby incorporated by reference herein.

With continuing reference to FIG. 1, the remote or cloud computing system 108 may be a proprietary remote/cloud computing system or a commercial cloud computing system. The remote/cloud computing system 108 may provide additional computing resources on-demand as needed when the computing resources of the computing device 106 are not sufficient. The computing device 106 and the remote/cloud computing system 108 may communicate with each other through a communication link 118, which may traverse one or more communication networks (not shown). The communication networks may include, with limitation, an Ethernet network, Wi-Fi network, a cellular network, a satellite network, an intranet, an extranet, the Internet, and/or the Internet backbone, among other types of networks. Persons skilled in the art will recognize implementations for the remote/cloud computing system 108 and how to interface with such systems through various types of networks. For example, the remote/cloud computing system 108 may include an array of processing circuitry (defined above) and may execute machine-readable instructions. Such implementations, interfaces, and networks are contemplated to be within the scope of the present disclosure.

Accordingly, an exemplary therapy delivery system has been described above. For convenience, the description below may primarily refer to an insulin delivery system as an example of the therapy delivery system. However, it is intended that any aspect, embodiment, or description relating to an insulin delivery system shall be applicable to a therapy delivery system which delivers a therapy other than insulin.

Aspects of the present disclosure relate to a graphical user interface for presenting physiological data over a historical time period. In aspects of the present disclosure, the graphical user interface also presents adjusted physiological data over portions of or all of the historical time period based on adjustments to historical events.

As mentioned in connection with FIG. 1, a therapy delivery system may store various data, such as sensed data of the monitoring system 104 and therapy delivery data of the delivery device 102, among other things. In various embodiments, the computing device 106 and/or the remote or cloud computing system 108 may store physiological information related to a particular person and event information related to the therapy delivery. Using insulin therapy as an example, a therapy delivery system may store physiological data such as sensed bodily glucose values; therapy delivery data such as time, type, and amount of insulin delivered; event information such as time and type of meal consumed as well as carbohydrates consumed; and physiological information such as a person's insulin sensitivity factor, insulin-to-carbohydrate ratio, rate of absorption of carbohydrates into the body, and rate of converting carbohydrates into glucose, among other things. Such stored data may be used to present physiological data and event information in a graphical user interface for a historical time period; allow a user to use the graphical user interface to adjust one or more historical events that occurred during the historical time period; determine adjusted physiological data based on the adjusted historical event(s); and present the adjusted physiological data over portions of or all of the historical time period in the graphical user interface. These aspects of the present disclosure will be described in more detail below. The data described above is exemplary, and other data is contemplated to be within the scope of the present disclosure.

Figure 2:
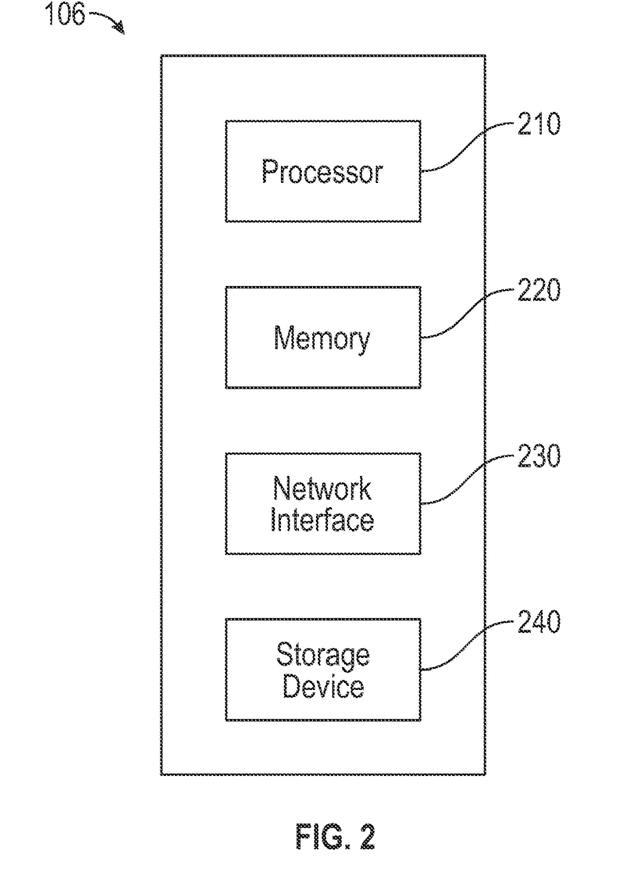
FIG. 2 is a block diagram illustrating exemplary components of a computing device, in accordance with aspects of the present disclosure.

Turning now to FIG. 2, a block diagram illustrating components of an exemplary computing device is shown. The illustrated computing device may be the computer device 106 of FIG. 1 or may be a different computing device, such as a person's smartphone, tablet, laptop, desktop computer, or augmented reality/virtual reality (AR/VR) headset, among other things. The computing device may present the graphical user interface mentioned above. For convenience, the illustrated computing device of FIG. 2 will be described as the computing device 106 of FIG. 1, but it is intended and will be understood that the following disclosure will apply to any computing device. The computing device 106 generally includes a processor 210, memory 220, a wireless network interface 230, and a storage device 240. The memory 220 and/or the storage device 240 may include instructions that, when executed by the processor 210, may cause the computing device 106 to perform the techniques disclosed herein.

In various aspects, the memory 220 may include random access memory, read-only memory, magnetic disk memory, solid-state memory, optical disc memory, and/or another type of memory. In various aspects, the processor 210 may be, without limitation, a digital signal processor, a microprocessor, an ASIC, a graphics processing unit ("GPU"), a field-programmable gate array ("FPGA"), or a central processing unit ("CPU"), or some combination of the foregoing. In various aspects, the memory 220 can communicate with the processor 210 through communication buses of a circuit board and/or through communication cables such as serial ATA cables or other types of cables. The memory 220 includes processor-readable instructions that are executable by the processor 210 to perform and/or control operations of the computing device 106.

In various aspects, and as shown in the embodiment of FIG. 2, the computing device 106 includes a wireless network interface 230 that is configured to communicate with other computing devices and/or computing systems, such as the remote or cloud computing system 108 of FIG. 1. In aspects, a storage device 240 may be used for storing data. For example, the data may include historical physiological data measured by the monitoring device 104, historical therapy delivery data provided by the delivery device 102, and/or other historical event information, such as meal and/or exercise information gathered and/or entered via computing device 106.

For the sake of clarity, other components of the computing device 106 are not shown in FIG. 2. Examples of such components include, but are not limited to, a display screen and/or a user input device (e.g., a touch screen, touchpad, mouse, AR/VR motion sensor, etc.). Persons skilled in the art will recognize such other components of a computing device, and they are contemplated to be within the scope of the present disclosure. As described below in connection with FIG. 4, a computing device can present a graphical user interface on a display screen and can receive user interactions with the graphical user interface by the user input device.

Figure 3:
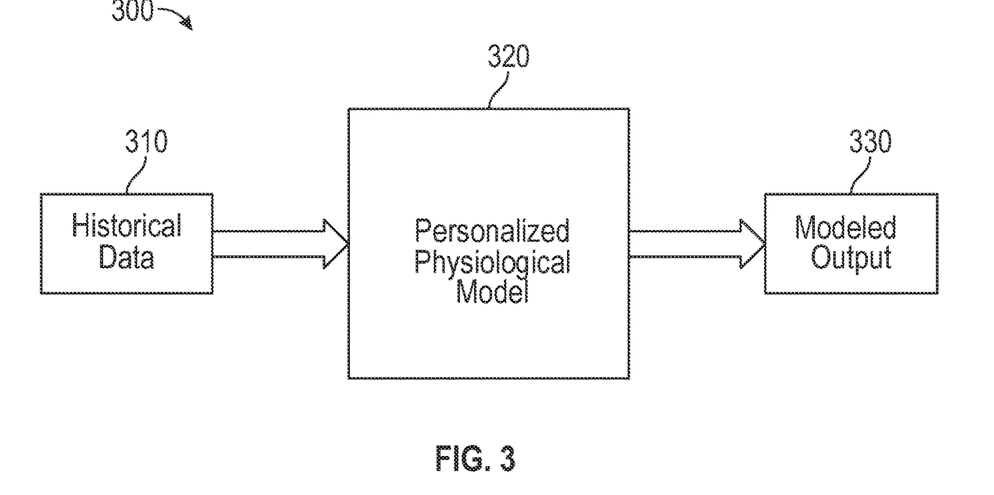
FIG. 3 is a block diagram illustrating an exemplary personalized physiological model, in accordance with aspects of the present disclosure.

Referring to FIG. 3, a block diagram 300 of an exemplary personalized physiological model 320 is shown. The personalized physiological model 320 may be a set of equations that can be used to simulate the physiological processes of a particular person. For example, in the diabetes field, model 320 may include equations for predicting the glycemic responses of a specific person to meals and/or insulin. The equations may be tailored to a particular person based on determining the values of coefficients used in the equations. In various embodiments, depending on the complexity of the personalized physiological model 320, all or a portion of the physiological model 320 can be stored on and/or applied by the computing device 106; and/or all or a portion of the physiological model 320 can be stored in and/or applied by a cloud or remote computing system (e.g., the remote/cloud computing system 108 of FIG. 1).

In various embodiments, the personalized physiological model 320 may be generated using machine learning techniques. In various embodiments, the machine learning techniques may involve one or more neural networks. A neural network may apply matrix processing operations to localized portions of a data set, and the results of those operations (which can involve dozens of different parallel and serial calculations) are used in training and utilizing neural networks. In aspects, the machine learning techniques may involve a combination of one or more deep learning neural networks which do not require feature engineering and/or one or more classical machine learning algorithms (e.g., support vector machine, decision tree, etc.) which involve some degree of feature engineering. In various embodiments, the machine learning techniques may involve a regression algorithm that provides output values of a continuous output variable. In various embodiments, the machine learning techniques may involve a classification algorithm that classifies input data to one or more output classes. Persons skilled in the art will recognize such machine learning techniques and how to implement them.

In aspects of the present disclosure, the personalized physiological model 320 of a person can be used to provide modeled physiological data 330 for the person. For example, the personalized physiological model may receive historical data as input data 310 and may output modeled physiological data 330. In the case of a personalized glycemic response model, event information/data, such as meal data, insulin delivery data, and/or physiological data, may be provided as input to the personalized physiological model 320. In various embodiments, the personalized physiological model 320 may output modeled bodily glucose values 330 for a person. The personalized physiological model 320 may be trained using sufficient historical data 310 for a person such that the model 320 is capable of accurately simulating bodily glucose values 330 for the person in various circumstances. The personalized physiological model 320 may be trained to simulate bodily glucose values 330 for the person over various time periods in the past or in the future. In various embodiments, the personalized physiological model 320 may provide modeled bodily glucose values 330 at regular intervals during a time period (e.g., every minute, every five minutes, or every ten minutes).

In accordance with aspects of the present disclosure, the personalized physiological model 320 may be used to determine and output adjusted physiological data 330 for a person over a portion of or all of a historical time period. As described in more detail in connection with FIG. 4, the adjusted physiological data 330 can be based on user input indicative of adjustment to a historical event which occurred during the historical time period. A person may use the graphical user interface depicted in FIG. 4 to adjust the historical event, and the personalized physiological model 320 may output adjusted physiological data, for a portion of or all of the historical time period, as though the adjusted historical event had occurred.

The aspects and embodiments provided in connection with FIG. 3 are exemplary, and variations are contemplated to be within the scope of the present disclosure. For example, in accordance with aspects of the present disclosure, a personalized physiological model may be generated using techniques other than machine learning techniques. Such and other variations are contemplated to be within the scope of the present disclosure.

Figure 4:
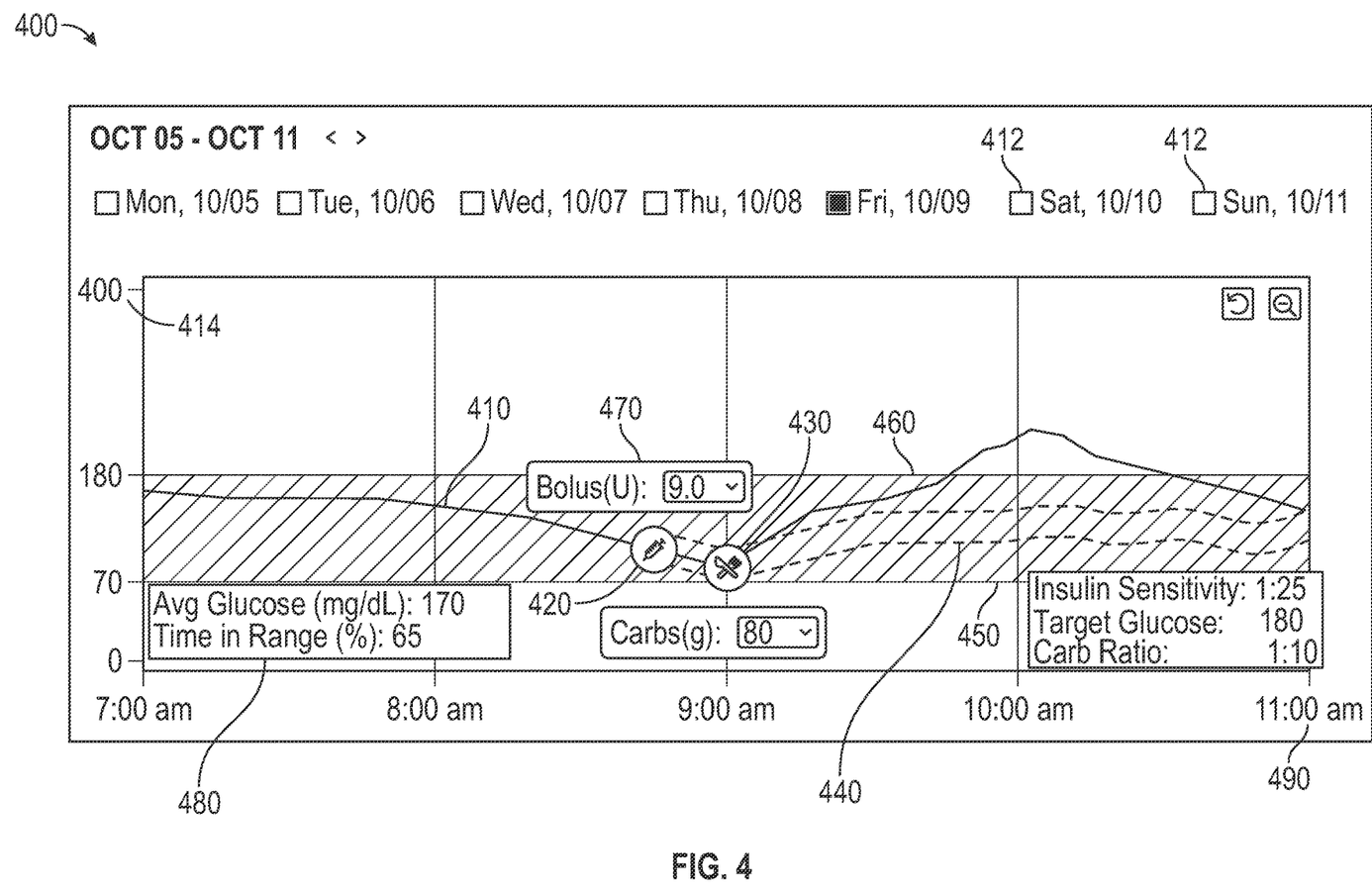
FIG. 4 is an exemplary graphical user interface, in accordance with aspects of the present disclosure.

Referring to FIG. 4, an exemplary graphical user interface (GUI) 400 is shown for presenting physiological data over a historical time period. The illustration provides an example in the field of diabetes, but it is intended and will be understood that the aspects and embodiments described in connection with FIG. 4 will be applicable to other fields. The GUI 400 can be presented on a display screen of a computing device (e.g., 106, FIG. 1). In various embodiments, an application executing on the computing device may provide the GUI 400. In various embodiments, a cloud or remote computing system (e.g., 108, FIG. 1) may serve or otherwise communicate the GUI 400 to the computing device (e.g., as a webpage or Software-as-a-Service, etc.) to be presented at the computing device. In various embodiments, data displayed by the GUI 400 may be stored at the computing device and/or may be stored at a cloud or remote computing system and communicated to the computing device.

In aspects of the present disclosure, the GUI 400 is configured to present a graph view of physiological data and events for a historical time period 490, which may be any time period in the past, such as an earlier time period in the same day, a time period in a previous day, or a time period in a previous week or year, among other time periods. In the illustrated GUI 400, the historical time period 490 spans 7:00 am to 11:00 am on October 9th, which is used merely as an example. The graph view may present, in a graphical format, values of historical physiological data 410 at various points in time during the historical time period 490 and may present, in a graphical format, one or more historical events 420, 430 that occurred at one or more points in time during the historical time period. In the illustrated example, the historical physiological data 410 is a person's sensed bodily glucose level 414 during the historical time period 490, and the historical event 430 is a meal consumed during the historical time period 490. A historical event 420, 430 can be plotted in the graph view at the time when the event 420, 430 occurred. In various embodiments, the event 420, 430 can be overlaid/plotted over the graphed historical physiological data 410, as shown in FIG. 4. In various embodiments, the event 420, 430 may be plotted apart from the graphed physiological data 410 (e.g., above or below the graphed historical physiological data 410).

In aspects of the present disclosure, the historical time period 490 may be adjustable. In aspects, the GUI 400 may include buttons 412 that are configured for changing a day and/or date range of the historical time period 490 for display. In aspects, the historical time period 490 may be adjusted to a later time period, to an earlier time period, to a longer time period, and/or to a shorter time period. A user may engage user input devices to adjust the historical time period 490 shown by the GUI 400, such as using gestures on a touch screen or touch pad (e.g., pinch, spread, or swipe gesture, etc.), motion sensing for a VR/AR system, dragging using a mouse, or using a mouse scroll wheel, among other things. In various embodiments, the historical time period 490 can be advanced forward or moved backward by swiping or dragging on the time indicator region of the historical time period 490 or on an open region of the graph view. In various embodiments, the historical time period 490 can be lengthened or reduced by using spread or pinch gestures or by using upward or downward scrolls of a mouse wheel, among other things. Such and other interactions for adjusting a historical time period 490 are contemplated to be within the scope of the present disclosure.

In accordance with aspects of the present disclosure, adjusting the historical time period 490 may automatically cause the GUI 400 to access and present historical physiological data and historical events corresponding to the adjusted historical time period. The GUI 400 may automatically redraw the graph view and may automatically rescale and/or relabel the historical time period 490 and/or the vertical axis 414. In various embodiments, to make the redrawing of the graph view appear instantaneous, the computing device which presents the GUI 400 may locally store or buffer a predetermined amount of historical physiological data and event data corresponding to time periods immediately before and after the displayed historical time period 490. This enables the locally stored data to be accessed and presented in a seemingly instantaneous manner. In case physiological data and event data is stored in a cloud or remote computing system, the computing device may request some or all of such data from the cloud or remote computing system and store it locally.

In various embodiments, the one or more historical events 420, 430 may include an exercise event of a person, a meal event of the person, and/or insulin delivery to the person, among other things. In accordance with aspects of the present disclosure, a user may adjust the timing of an event from one time point in the historical time period 490 to another time point in the historical time period 490. This enables exploring scenarios different from what actually occurred during the historical time period 490. For example, the timing of the event 430 may be adjusted (e.g., dragged) from about 9:00 AM, as shown in FIG. 4, to another time point in the historical time period 490 to explore a scenario in which the meal is consumed at a different time. A user may adjust the timing of an event by issuing voice commands; using a hold-and-move gesture on a touch screen, touch pad, or VR/AR system; or by using a mouse to click and drag, among other things. In the illustration of FIG. 4, the timing of an insulin bolus event 420 has been adjusted from its original time point to the illustrated time point, which may be about 8:45 am. In various embodiments, the GUI 400 may operate to restrict placement of an event anywhere other than at a point along the line of plotted historical physiological data 410. For example, when a user drags a marker for the insulin delivery event 420 to the left or right, the GUI 400 may display the marker for the event 420 to the left or right along the line of plotted historical physiological data 410 even if the user does not trace the line while dragging the marker for the event 420. The functionality provided by the GUI 400 for dragging an event provides an effective and efficient way for a user to adjust a historical event to explore scenarios different from what actually occurred during the historical time period. In various embodiments, a button in the GUI 400 may be used to reset the graph view and reset all adjusted events to the historical events that actually occurred during the historical time period. Such and other embodiments are contemplated to be within the scope of the present disclosure.

The one or more historical events 420, 430 may include one or more event attributes, such as quantity (e.g., of insulin doses and/or meal portions), intensity, duration (e.g., meal duration, exercise duration), and/or content (e.g., meal carbohydrate amount), among other things. In the illustrated example, the adjusted marker for the event 420 is an insulin delivery event and an attribute is bolus size. In accordance with aspects of the present disclosure, one or more event attributes may be displayed by the GUI 400, such as in a dialog box or in other GUI display elements that persons skilled in the art will recognize. For example, in FIG. 4, GUI 400 displays the event attribute 470 for the insulin delivery event 420. In various embodiments, the event attribute 470 may be displayed near the marker for the event 420. In various embodiments, the event attribute 470 may be displayed when a user interacts with the marker for the event 420, such as by tapping or dragging on a touch screen, touch pad, or AR/VR system; or by a mouse pointer hovering over, clicking, or dragging the marker for the event 420. In such embodiments, a displayed event attribute 470 may disappear after a predetermined amount of time, such as five seconds or eight seconds, or another time duration. In the example of FIG. 4, the displayed event attribute 470 provides a user interface for a user to change the value of the attribute. The user interface may be, for example, a pull-down list user interface, a number input user interface, and/or a rotating wheel user interface, among other things.

In various embodiments, the functionality of adjusting an event (e.g., adjusting the timing and/or an attribute of an event) provides an effective and efficient way for a user to explore scenarios different from what actually occurred during the historical time period 490. In accordance with aspects of the present disclosure, responsive to detecting adjustment of an event, such as dragging of the marker for event 420, the GUI 400 presents adjusted physiological data 440 determined based on providing the adjustment as input to a physiological model. As shown in FIG. 4, the adjusted physiological data 440 may be presented as a range of possible physiological data values having a range upper bound and a range lower bound over the historical time period 490. Continuing with the example in the diabetes field, the adjusted physiological data 440 may reflect bodily glucose levels for a person resulting from the adjusted event 420. The adjusted physiological data 440 may be presented over a portion of the historical time period 490 or all of the historical time period 490, depending on the circumstances. In various embodiments, the adjusted physiological data 440 may, at the least, be displayed from the time point of the adjusted event 420 to the end of the historical time period 490, as shown in FIG. 4.

As mentioned above, the adjusted physiological data 440 may be determined using a personalized physiological model 320, such as that shown and described in connection with FIG. 3. In various embodiments, all or part of the data processing for generating adjusted physiological data and/or other data presented by the GUI 400 may be performed by the computing device (e.g., 106, FIG. 1) and/or the cloud or remote computing system (e.g., 108, FIG. 1). For example, computing device 106 may locally store historical data and a physiological model so that computing device 106 can locally determine adjusted physiological data and display it via GUI 400. Alternatively, computing device 106 may communicate an event adjustment to remote computing system 108, which determines adjusted physiological data that can be obtained and displayed by computing device 106.

In aspects of the present disclosure, the adjusted physiological data 440 may be dynamically determined and displayed in the GUI 400 during an event adjustment (e.g., as the marker for the event 420 is being dragged). Thus, the GUI 400 may be dynamically refreshed to redraw the graph view with the adjusted physiological data 440. In various embodiments, the redrawing of the graph view with the adjusted physiological data 440 is performed such that continuously adjusting the marker for an event (e.g., slowly moving the marker for an event across a plurality of points in time with an uninterrupted motion) results in an animation-like movement of the adjusted physiological data 440 through a range of values corresponding to the plurality of points in time. More generally, while a marker for an event is being adjusted (e.g., dragged) from a first position in the graph view to a second position in the graph view, adjusted physiological data 440 may be successively accessed and displayed for each of a number of positions between the first position and the second position. In this manner, the successive display of the adjusted physiological data 440 for the positions between the first position and the second positions provides an animation-like presentation of the adjusted physiological data 440 while the marker for the event is being adjusted (e.g., dragged).

In aspects of the present disclosure, the GUI 400 may display further information related to physiological data, event information, the personalized physiological model (320, FIG. 3), and/or other information, such as an insulin sensitivity value, a target glucose value, and/or a carbohydrate ratio. In various embodiments, the GUI 400 may display analyzed information 480 (e.g., average glucose value and time in range) and may display a graphical illustration relating to the upper and lower bounds 460, 450 for a target range. Although these examples relate to the field of diabetes, it should be appreciated that information relating to other fields are contemplated to be within the scope of the present disclosure. In various embodiments, the analyzed information 480 may be updated as an event is adjusted such that the analyzed information 480 may change continuously in response to a continuous movement of an event marker.

In various embodiments, a menu of events may be available to a user and may be used to introduce additional events into the graph view. For example, the marker for the insulin delivery event 420 may not have been adjusted but, rather, may have been added to the graph view as a new event selected from a menu of events. Such and other variations are contemplated to be within the scope of the present disclosure.

Figure 5:
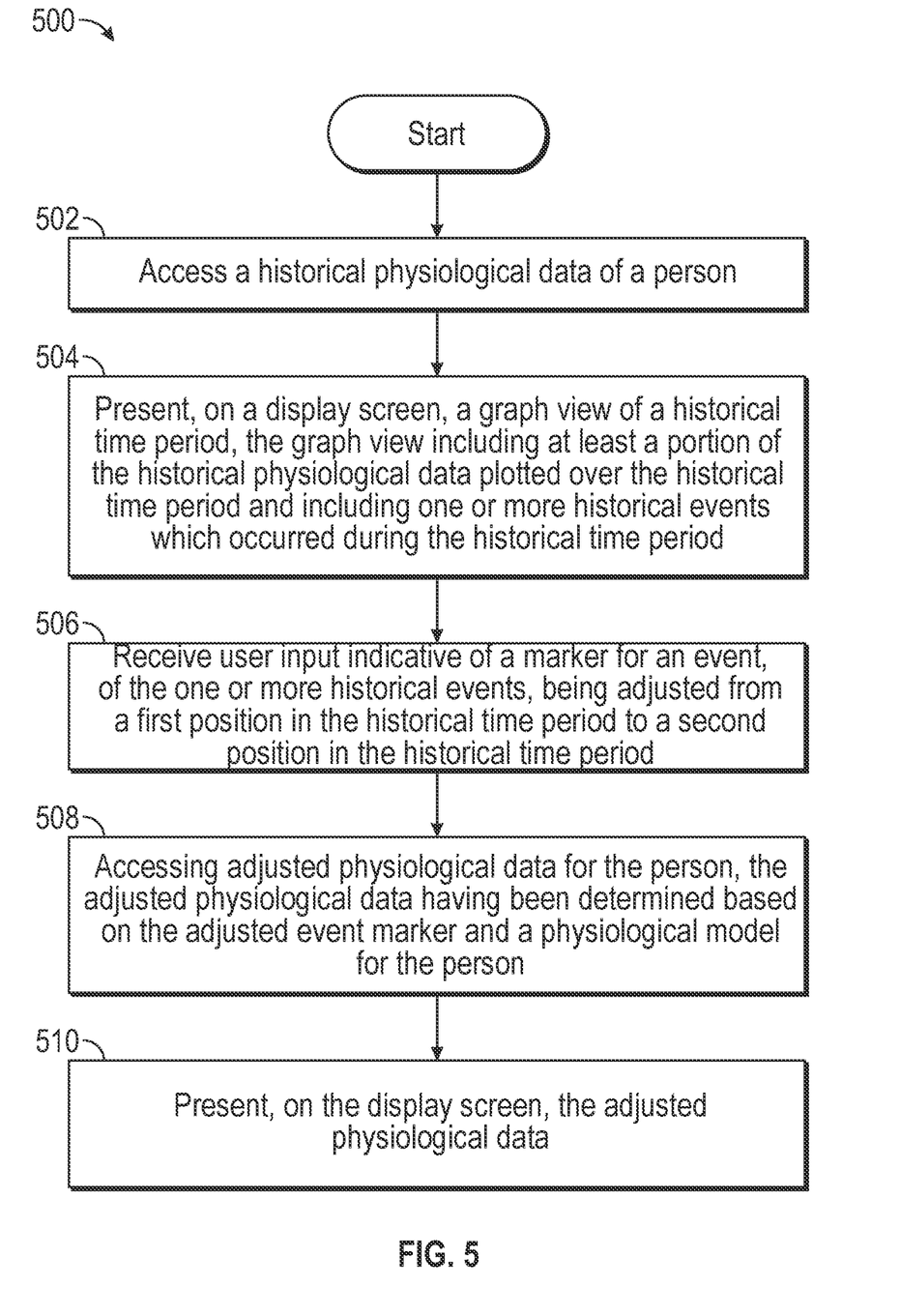
FIG. 5 is a flow diagram illustrating exemplary techniques related to dynamic adjustments of physiological data, in accordance with aspects of the present disclosure.

Referring to FIG. 5, a flow diagram 500 depicts example techniques related to dynamic adjustments of physiological data. Although the example of FIG. 5 depicts a particular order, it should be appreciated that the techniques may be performed in a different order. Furthermore, the present disclosure contemplates variations in which one or more parts of the diagram 500 are modified (e.g., omitted and/or supplemented). For example, the example of FIG. 5 may be modified for performance by a computing device 106 (FIG. 2) and/or a cloud computing system (e.g., 108, FIG. 1). These variations are contemplated to be within the scope of the present disclosure.

At block 502, historical physiological data of a person is accessed. The historical physiological data may be physiological data for a predetermined time period in the past. For example, the computing device 106 may access glycemic response data of the person for the past week from local memory and/or from cloud computing system 108. Additionally, other personal data (e.g., historical event data) for the predetermined time period may be accessed. The duration of the predetermined time period may be determined based on default settings and/or user input.

At block 504, a graph view of a historical time period (e.g., a subset of the predetermined time period) is presented on a display screen (e.g., via GUI 400 implemented on a display screen of computing device 106). The graph view includes at least a portion of the historical physiological data plotted over the historical time period and includes one or more historical events (e.g., 430, FIG. 4) which occurred during the historical time period. For example, the graph view may include glycemic response data plotted over one day of the past week and one or more events which occurred during that one day. The one or more events may include a historical meal event for the person and/or historical insulin delivery event for the person. In aspects, the graph view may include event attributes 470 for the one or more events 420, 430. The attributes 470 may include timing, size (e.g., of insulin doses and/or meals), intensity, duration (e.g., exercise duration), and/or content (e.g., meal carbohydrate amount). For example, the computing device 106 may present to a patient his/her historical glycemic response data plotted over time with logged events overlaid on the plotted data.

At block 506, user input indicative of an event marker being adjusted is received. The event marker is a marker for an event of the one or more historical events 420, 430. The event marker is adjusted from a first position in the historical time period to a second position in the historical time period. The second position may correspond to a time point in the historical time period that is displayed in the graph view. For example, the computing device 106 may receive, via the GUI 400, user input indicative of a patient and/or a health care professional moving the marker for event 420 to a point in time 15 minutes earlier or 15 minutes later.

At block 508, adjusted physiological data is accessed (e.g., by computing device 106 from local memory and/or from cloud computing system 108). The adjusted physiological data is determined (e.g., by computing device 106 and/or by cloud computing system 108) based on the adjusted event marker and a physiological model for the person. The adjusted physiological data may be determined for a time period starting at the second position and ending at the end of the historical time period that is displayed in the graph view.

For example, the adjusted physiological data may include adjusted glycemic response data that was determined based on adjustment of the timing of an insulin delivery event. The adjusted timing may be provided as input to personalized physiological model 320 (FIG. 3), which may generate the adjusted glycemic response data as output. The adjusted glycemic response data may include glycemic response data for the time period starting at time point corresponding to the adjusted timing and ending at the end of historical time period displayed via GUI 400.

At block 510, the adjusted physiological data is presented (e.g., via GUI 400 implemented on a display screen of computing device 106). In aspects, the adjusted physiological data may be presented along with the physiological data that was presented prior to event adjustment.

The embodiments disclosed herein are merely provided as examples. Although certain embodiments are described herein as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described operations, methods, programs, algorithms, or codes may be converted to, or expressed in, a programming language or computer program embodied on a computer, processor, or machine-readable medium. The terms "programming language" and "computer program," as used herein, each include any language used to specify instructions to a computer or processor, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages that are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. To the extent consistent, any or all of the aspects detailed herein may be used in conjunction with any or all of the other aspects detailed herein. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A device comprising:
one or more processors; and
one or more processor-readable storage media storing instructions which, when executed by the one or more processors, cause performance of:
accessing historical physiological data of a person, wherein the historical physiological data comprises sensed data;
presenting, on a display screen, a graph view of a historical time period, the graph view including at least a portion of a line of the historical physiological data plotted over the historical time period and including one or more historical events which occurred during the historical time period;
receiving user input indicative of a marker for an event, of the one or more historical events, being adjusted from a first position in the historical time period to a second position in the historical time period, the second position corresponding to a time point in the historical time period, wherein the first position and the second position are both on the line of the historical physiological data;
responsive to receiving the user input, accessing adjusted historical physiological data for the person from at least the time point in the historical time period to an end of the historical time period, the adjusted historical physiological data having been determined based on the historical physiological data, the adjusted marker for the event, and a physiological model for the person; and
presenting, on the display screen, the adjusted historical physiological data.

2. The device of claim 1, wherein the one or more historical events includes at least one of: a meal event of the person or insulin delivery event of the person.

3. The device of claim 1, wherein the user input indicative of the marker for the event being adjusted from the first position to the second position is a user input indicative of the marker for the event being dragged from the first position to the second position.

4. The device of claim 3, wherein the one or more processor-readable storage media store further instructions which, when executed by the one or more processors, cause performance of, while the marker for the event is dragged from the first position to the second position, for each position of a plurality of positions between the first position and the second position:
accessing respective adjusted historical physiological data for the person; and
presenting, on the display screen, the respective adjusted historical physiological data.

5. The device of claim 4, wherein presenting the respective adjusted historical physiological data for each position of the plurality of positions between the first position and the second position comprises providing an animation-like presentation by successively displaying the adjusted historical physiological data corresponding to the plurality of positions between the first position and the second position.

6. The device of claim 3, wherein the one or more processor-readable storage media store further instructions which, when executed by the one or more processors, cause performance of, while the marker for the event is dragged from the first position to the second position, for each position of a plurality of positions between the first position and the second position:
presenting the marker for the event overlaid over a respective portion of the historical physiological data corresponding to respective position.

7. A processor-implemented method comprising:
accessing historical physiological data of a person, wherein the historical physiological data comprises sensed data;
presenting, on a display screen, a graph view of a historical time period, the graph view including at least a portion of a line of the historical physiological data plotted over the historical time period and including one or more historical events which occurred during the historical time period;
receiving user input indicative of a marker for an event, of the one or more historical events, being adjusted from a first position in the historical time period to a second position in the historical time period, the second position corresponding to a time point in the historical time period, wherein the first position and the second position are both on the line of the historical physiological data;
responsive to receiving the user input, accessing adjusted historical physiological data for the person from at least the time point in the historical time period to an end of the historical time period, the adjusted historical physiological data having been determined based on the historical physiological data, the adjusted marker for the event, and a physiological model for the person; and
presenting, on the display screen, the adjusted historical physiological data.

8. The processor-implemented method of claim 7, wherein the one or more historical events includes at least one of: a meal event of the person or insulin delivery data of the person.

9. The processor-implemented method of claim 7, wherein the user input indicative of the marker for the event being adjusted from the first position to the second position is a user input indicative of the marker for the event being dragged from the first position to the second position.

10. The processor-implemented method of claim 9, further comprising, while the marker for the event is dragged from the first position to the second position, for each position of a plurality of positions between the first position and the second position:
accessing respective adjusted historical physiological data for the person; and
presenting, on the display screen, the respective adjusted historical physiological data.

11. The processor-implemented method of claim 10, wherein presenting the respective adjusted historical physiological data for each position of the plurality of positions between the first position and the second position comprises providing an animation-like presentation by successively displaying the adjusted historical physiological data corresponding to the plurality of positions between the first position and the second position.

12. The processor-implemented method of claim 9, further comprising, while the marker for the event is dragged from the first position to the second position, for each position of a plurality of positions between the first position and the second position:
presenting the marker for the event overlaid over a respective portion of the historical physiological data corresponding to respective position.

13. One or more non-transitory processor-readable storage media storing instructions which, when executed by one or more processors, cause performance of:
accessing a historical physiological data of a person, wherein the historical physiological data comprises sensed data;
presenting, on a display screen, a graph view of a historical time period, the graph view including at least a portion of a line of the historical physiological data plotted over the historical time period and including one or more historical events which occurred during the historical time period;
receiving user input indicative of a marker for an event, of the one or more historical events, being adjusted from a first position in the historical time period to a second position in the historical time period, the second position corresponding to a time point in the historical time period, wherein the first position and the second position are both on the line of the historical physiological data;
responsive to receiving the user input, accessing adjusted historical physiological data for the person from at least the time point in the historical time period to an end of the historical time period, the adjusted historical physiological data having been determined based on the historical physiological data, the adjusted marker for the event, and a physiological model for the person; and
presenting, on the display screen, the adjusted historical physiological data.

14. The one or more non-transitory processor-readable storage media of claim 13, wherein the one or more historical events includes at least one of: a meal event of the person or insulin delivery data of the person.

15. The one or more non-transitory processor-readable storage media of claim 13, wherein the user input indicative of the marker for the event being adjusted from the first position to the second position is a user input indicative of the marker for the event being dragged from the first position to the second position.

16. The one or more non-transitory processor-readable storage media of claim 15, further storing instructions which, when executed by the one or more processors, cause performance of, while the marker for the event is dragged from the first position to the second position, for each position of a plurality of positions between the first position and the second position:
accessing respective adjusted historical physiological data for the person; and
presenting, on the display screen, the respective adjusted historical physiological data.

17. The one or more non-transitory processor-readable storage media of claim 16, wherein presenting the respective adjusted historical physiological data for each position of the plurality of positions between the first position and the second position comprises providing an animation-like presentation by successively displaying the adjusted historical physiological data corresponding to the plurality of positions between the first position and the second position.

18. The one or more non-transitory processor-readable storage media of claim 15, further storing instructions which, when executed by the one or more processors, cause performance of, while the marker for the event is dragged from the first position to the second position, for each position of a plurality of positions between the first position and the second position:

presenting the marker for the event overlaid over a respective portion of the historical physiological data corresponding to respective position.

\* \* \* \* \*